United States Patent
Kitamura

(10) Patent No.: US 11,009,518 B2
(45) Date of Patent: May 18, 2021

(54) APPARATUS AND METHOD FOR AUTOMATED ANALYSIS

(71) Applicant: JEOL Ltd., Tokyo (JP)

(72) Inventor: Takeshi Kitamura, Tokyo (JP)

(73) Assignee: JEOL Ltd.

( * ) Notice: Subject to any disclaimer, the term of this patent is extended or adjusted under 35 U.S.C. 154(b) by 240 days.

(21) Appl. No.: 16/208,757

(22) Filed: Dec. 4, 2018

(65) Prior Publication Data

US 2019/0170778 A1 Jun. 6, 2019

(30) Foreign Application Priority Data

Dec. 5, 2017 (JP) .............................. JP2017-233081

(51) Int. Cl.
| | |
|---|---|
| *G01N 35/02* | (2006.01) |
| *G01N 33/50* | (2006.01) |
| *G01N 35/00* | (2006.01) |
| *G01N 35/04* | (2006.01) |
| *G01N 35/10* | (2006.01) |

(Continued)

(52) U.S. Cl.
CPC ......... *G01N 35/025* (2013.01); *B67B 3/2033* (2013.01); *B67C 7/004* (2013.01); *G01N 33/50* (2013.01); *G01N 35/00584* (2013.01); *G01N 35/00732* (2013.01); *B01L 2300/021* (2013.01);

(Continued)

(58) Field of Classification Search
CPC .................. G01N 35/025; G01N 33/50; G01N 35/00584; G01N 35/00732; G01N 2035/0439; B67B 3/2033; B67C 7/004
See application file for complete search history.

(56) References Cited

U.S. PATENT DOCUMENTS

| | | | |
|---|---|---|---|
| 7,311,223 B2* | 12/2007 | Post ..................... | B01F 13/1058 222/1 |
| 2004/0258565 A1* | 12/2004 | Watari ............... | G01N 35/1002 422/64 |
| 2017/0227563 A1* | 8/2017 | Nishigaki .......... | G01N 35/1004 |

FOREIGN PATENT DOCUMENTS

| | | |
|---|---|---|
| JP | 618968 U | 3/1994 |
| JP | H0618968 U * | 3/1994 |

(Continued)

OTHER PUBLICATIONS

Translation of JP2008267830A, Kase, Kimihiro, Nov. 6, 2008 (Year: 2008).*

(Continued)

*Primary Examiner* — Jill A Warden
*Assistant Examiner* — Henry H Nguyen
(74) *Attorney, Agent, or Firm* — The Webb Law Firm

(57) ABSTRACT

There is provided an automated analyzer which can eliminate static charge on receptacles storing analytes or reagents to thereby offer improved accuracy of analysis. The automated analyzer comprises: a receptacle carrier mechanism operative to hold a plurality of receptacles storing liquid and to carry the held receptacles in a given direction; a reader device for reading identification information of the receptacles carried by the receptacle carrier mechanism; a static eliminator for eliminating static charge on the receptacles carried by the receptacle carrier mechanism; and an input/output controller for causing the static eliminator to carry out the elimination of the static charge in synchronism with successive reading by the reader device of the identification information of the receptacles carried by the receptacle carrier mechanism.

10 Claims, 6 Drawing Sheets

(51) Int. Cl.
 *B67B 3/20* (2006.01)
 *B67C 7/00* (2006.01)
(52) U.S. Cl.
 CPC .............. *G01N 2035/00752* (2013.01); *G01N 2035/0439* (2013.01); *G01N 2035/1025* (2013.01)

(56) References Cited

FOREIGN PATENT DOCUMENTS

| | | | | | |
|---|---|---|---|---|---|
| JP | 2001004640 | A | * | 1/2001 | |
| JP | 2007309742 | A | * | 11/2007 | |
| JP | 2008102032 | A | * | 5/2008 | |
| JP | 2008267830 | A | * | 11/2008 | |
| JP | 2017146251 | A | * | 8/2017 | |
| WO | WO-2015045461 | A1 | * | 4/2015 | ............. G01N 35/04 |

OTHER PUBLICATIONS

Translation of JP2008102032A, Mori, Yasuo, May 1, 2008 (Year: 2008).*
Translation of JP2007309742A, Matsushita, Atsushi, Nov. 29, 2007 (Year: 2007).*

* cited by examiner

APPARATUS AND METHOD FOR AUTOMATED ANALYSIS

CROSS-REFERENCE TO RELATED APPLICATION

This application claims priority to Japanese Patent Application No. 2017-233081 filed Dec. 5, 2017, the disclosure of which is hereby incorporated in its entirety by reference.

BACKGROUND OF THE INVENTION

Field of the Invention

The present invention relates to an apparatus and method for automated analysis.

Description of Related Art

Biochemical analyzers for analyzing biogenic substances contained in analytes such as blood and urine are known as one type of automated analyzer. In such an automated analyzer, an analyte received in an analyte receptacle and a reagent received in a reagent receptacle are pipetted into a reaction receptacle and mixed together in the reaction receptacle to cause them to react together.

One example of such an automated analyzer is proposed in JP-UM-A-6-18968 and has a structure including a static eliminator mounted in a reaction receptacle transfer path at a location ahead of the pipetting position of a pipette mechanism for analyte sample or reagent to electrically neutralize static charge on the surface of the reaction receptacle.

Patent Documents

Patent document 1: JP-UM-A-6-18968

However, with the automated analyzer of the structure described above, static charge on the analyte receptacle and reagent receptacle in which an analyte and a reagent are respectively already received cannot be eliminated because the analyzer is intended to eliminate static charge on a hollow reaction receptacle into which analyte and reagent are not yet aliquotted. Consequently, it is difficult to prevent deterioration of the accuracy of analysis due to static charge, for example, on the analyte receptacle and on the reagent receptacle.

SUMMARY OF THE INVENTION

Accordingly, it is an object of the present invention to provide an apparatus and method for automated analysis which can eliminate static charge on receptacles in which analyte or reagent is already received, to thereby provide improved accuracy of analysis.

This object is achieved in accordance with the teachings of the present invention by providing an automated analyzer comprising: a receptacle carrier mechanism operative to hold a plurality of receptacles storing liquid and to carry the held receptacles in a given direction; a reader device for reading identification information of the receptacles carried by the receptacle carrier mechanism; a static eliminator for eliminating static charge on the receptacles carried by the receptacle carrier mechanism; and a controller for causing the static eliminator to carry out the elimination of the static charge in synchronism with successive reading by the reader device of the identification information of the receptacles carried by the receptacle carrier mechanism.

According to the present invention configured as described so far, static charge on the receptacle storing liquid such as analyte or reagent can be eliminated. Consequently, automated analyzer and automated analysis method capable of providing improved accuracy of analysis can be offered.

DESCRIPTION OF THE INVENTION

Embodiments of the automated analyzer and automated analysis method of the present invention are hereinafter described in detail with reference to the drawings.

First Embodiment

<<Automated Analyzer>>

Figure 1:
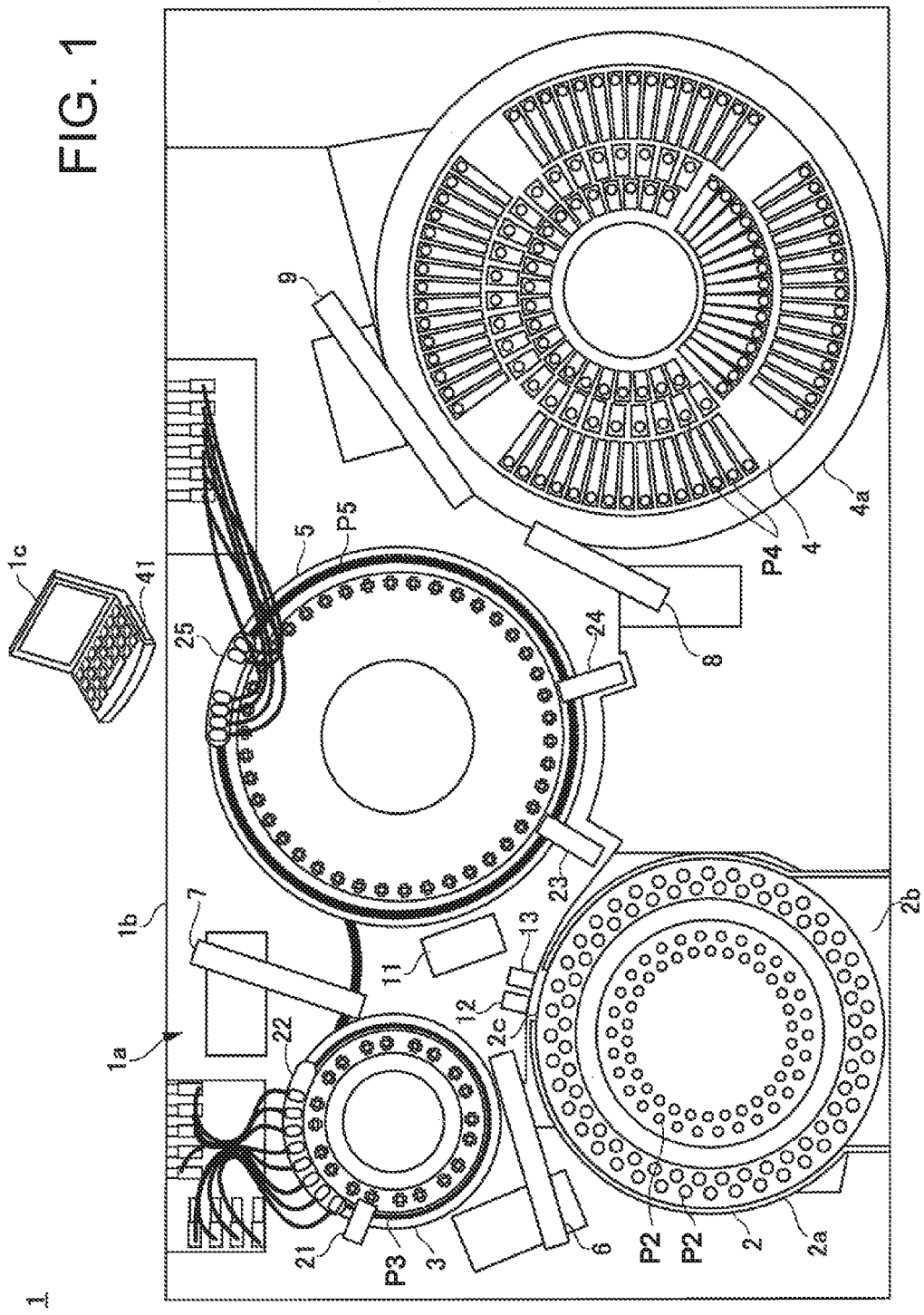
FIGS. 1 and 2 are schematic representations of an automated analyzer associated with a first embodiment of the present invention, illustrating different operational states of the analyzer.
Figure 2:
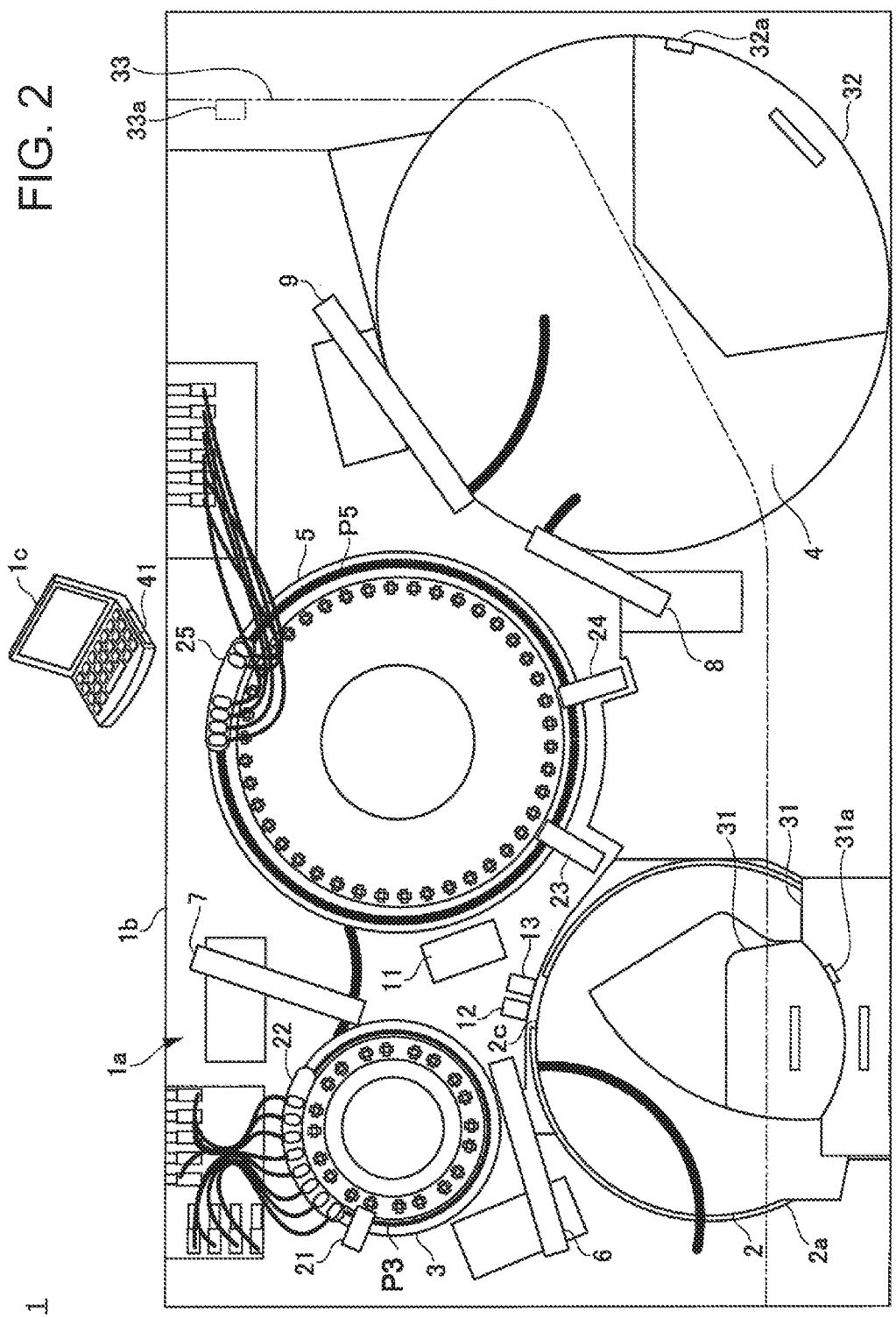

FIGS. 1 and 2 are schematic representations of an automated analyzer associated with a first embodiment of the present invention, showing different operational states of the analyzer. The automated analyzer, generally indicated by reference numeral 1, is a biochemical analyzer for analyzing biogenic substances contained in an analyte such as blood and urine and includes a measuring section 1a, an enclosure 1b, and a control section 1c.

Among these, the measuring section 1a has a mechanical drive mechanism including a sample turntable 2, a dilution turntable 3, a reagent turntable 4, and a reaction turntable 5. Also, the measuring section 1a has drive mechanisms including a sample diluting pipette 6, a sampling pipette 7, a first reagent pipette 8, and a second reagent pipette 9. Besides these drive mechanisms, the measuring section 1a includes a photometer 11, a reader device 12, a static eliminator 13.

The enclosure 1b accommodates the measuring section 1a and includes a first cover member 31, a second cover member 32, and a third cover member 33 as shown in FIG. 2. In the state of FIG. 1, the first cover member 31, the second cover member 32, and the third cover member 33 of the enclosure 1b have been taken off.

The control section 1c includes a manual control unit 41. In addition, the control section 1c includes a memory (not shown in this figure) and an input/output controller (not shown in this figure). The components of these sections (i.e., the measuring section 1a, enclosure 1b, and control section 1c) are described in detail below.

Measuring Section 1a

<Sample Turntable 2>

The sample turntable 2 is another receptacle carrier mechanism and serves to hold plural rows of analyte receptacles P2 along the outer peripheral edge of a disk and to transport the held analyte receptacles P2 in both circumferential directions. Each analyte receptacle P2 held on the sample turntable 2 is a container for storing an analyte to be examined. Each analyte receptacle P2 is in a tubular form having a closed bottom portion on its one side. Each individual analyte receptacle P2 possesses unique identification information. One example of the identification information is a barcode attached to the sidewall of the analyte receptacle P2.

The sample turntable 2 holds these analyte receptacles P2 under vertical conditions. The sidewall of each held analyte receptacle P2 is exposed to be viewable from the radially outer side. Where the sample turntable 2 is installed in a substantially cylindrical receiving wall 2a formed in the enclosure 1b, openings 2b and 2c may be formed in the receiving wall 2a as the need arises. The sidewall of each analyte receptacle P2 is visibly exposed through the openings 2b and 2c.

<Dilution Turntable 3>

The dilution turntable 3 is a further receptacle carrier mechanism and operative to hold a plurality of dilution receptacles P3 along the outer periphery of a disk and to transport the held dilution receptacles P3 in both circumferential directions. Analyte is aspirated from the analyte receptacles P2 that are disposed on the sample turntable 2. Then, the aspirated analyte is diluted and dispensed into the dilution receptacles P3 held on the dilution turntable 3.

A stirrer 21 and a cleaner 22 are arranged around the dilution turntable 3. The stirrer 21 is a device for stirring together an analyte and a diluent in each dilution receptacle P3. The cleaner 22 is a device for cleaning each dilution receptacle P3 after diluted analyte has been drawn in by a sampling pipette (described below).

<Reagent Turntable 4>

The reagent turntable 4 is an additional receptacle carrier mechanism and operates to hold a plurality of reagent receptacles P4 along the outer periphery of a disk and to transport the held reagent receptacles P4 in both circumferential directions. Reagent is received in the reagent receptacles P4 that are held on the reagent turntable 4. The reagent turntable 4 is installed inside a cylindrical thermostat bath 4a so that each reagent receptacle P4 is cooled and kept at a low temperature at all times.

<Reaction Turntable 5>

The reaction turntable 5 is a further receptacle carrier mechanism and disposed between the dilution turntable 3 and the reagent turntable 4. The reaction turntable 5 operates to hold a plurality of reaction receptacles P5 along the outer periphery of a disk and to transport the held reaction receptacles P5 in both circumferential directions. A given amount of the diluted analyte sampled from a selected one of the dilution receptacles P3 on the dilution turntable 3 and a given amount of a reagent sampled from a selected one of the reagent receptacles P4 on the reagent turntable 4 are pipetted into each reaction receptacle P5 held on the reaction turntable 5. Inside the reaction receptacle P5, the diluted analyte and the reagent are stirred together to induce a reaction.

This reaction turntable 5 is so configured that the temperature of each reaction receptacle P5 is kept constant at all times by means of a thermostat bath (not shown). Around the reaction turntable 5, there are two stirrers 23 and 24 and a cleaner 25. Each of the stirrers 23 and 24 is a device for stirring together a diluted analyte and a reagent in a corresponding one of the reaction receptacles P5 held on the reaction turntable 5. The cleaner 25 is a device for cleaning the inside of each reaction receptacle P5 for which an inspection is complete.

<Sample Diluting Pipette 6>

The sample diluting pipette 6 is disposed close both to the sample turntable 2 and to the dilution turntable 3. The sample diluting pipette 6 has a liquid level sensor (not shown) which detects the heightwise position of the liquid level relative to the tip of the pipette, for example, by utilizing an electrostatic capacitance between the liquid level and the tip of the pipette. The sample diluting pipette 6 inserts its tip into a selected one of the analyte receptacles P2 held on the sample turntable 2 by a diluting pipette drive mechanism (not shown) until the tip reaches a given depth below the liquid level of analyte detected by the liquid level sensor. Then, a given amount of analyte is aspirated from the tip of the pipette that is filled with diluent. The sample diluting pipette 6 inserts its tip into a selected one of the dilution receptacles P3 on the dilution turntable 3 and dispenses the aspirated analyte and a given amount of diluent (e.g., physiological salt solution) supplied from the diluting pipette 6 itself into the dilution receptacle P3. As a result, in the dilution receptacle P3, the analyte is diluted by a given dilution factor such that an ultimate concentration of analyte is obtained. Then, the sample diluting pipette 6 is cleaned with a cleaner (not shown).

<Sampling Pipette 7>

The sampling pipette 7 is disposed close both to the dilution turntable 3 and to the reaction turntable 5. The sampling pipette 7 inserts its tip into the dilution receptacle P3 held on the dilution turntable 3 by the sampling pipette drive mechanism (not shown) and draws in a given amount of diluted analyte from the tip of the pipette filled with diluent. Then, the sampling pipette 7 dispenses the aspirated diluted analyte into a selected one of the reaction receptacles P5 on the reaction turntable 5 and injects the diluted analyte into the reaction receptacle P5.

<First Reagent Pipette 8 & Second Reagent Pipette 9>

The first reagent pipette 8 and the second reagent pipette 9 are positioned close both to the reagent turntable 4 and to the reaction turntable 5. Each of the first reagent pipette 8 and second reagent pipette 9 is equipped with a liquid level sensor (not shown) which detects the heightwise position of the liquid level relative to the tip of the pipette, for example, by utilizing an electrostatic capacitance between the liquid level and the tip of the pipette. Each of these reagent pipettes 8 and 9 inserts its tip into a selected one of the reagent receptacles P4 held on the reagent turntable 4 by a pipette drive mechanism (not shown) until the tip reaches a given depth below the liquid level of reagent detected by the liquid level sensor. Then, a given amount of reagent is aspirated from the tip of the pipette that is filled with diluent. Each of the reagent pipettes 8 and 9 dispenses the aspirated reagent into a selected one of the reaction receptacles P5 held on the reaction turntable 5.

<Photometer 11>

The photometer 11 makes optical measurements of the diluted analyte that has reacted with a drug solution inside the reaction receptacle 5, outputs numerical data indicative of the "absorbances" of the amounts of various components of the analyte, and detects the state of reaction of the diluted analyte. This photometer 11 is a multi-wavelength photometer, for example, which is so arranged around the reaction turntable 5 that its sensitive surface is directed at the center of rotation of the reaction turntable 5.

<Reader Device 12>

The reader device 12 is a device for reading identification information of the analyte receptacles P2 held on the sample turntable 2. If the identification information is in the form of a barcode, the reader device 12 is a barcode reader. This reader device 12 is so positioned around the sample turntable 2 that the reader head faces the center of rotation of the sample turntable 2. Especially, where the sample turntable 2 is positioned within the receiving wall 2a, the reader device 12 should be placed opposite to the peripheral walls of some of the analyte receptacles P2 held on the sample turntable 2 through the opening 2c formed in the receiving wall 2a.

<Static Eliminator 13>

The static eliminator 13 is a device for electrically neutralizing (and thus removing) static charge induced on each analyte receptacle P2 held on the sample turntable 2. This static eliminator 13 may be of the ionizer type, moistening type, or any other type. Where contamination of the measuring section 1a including the analyte receptacles P2 is considered, it is desired that the static eliminator 13 be of the ionizer type. Furthermore, with respect to its configuration, it is desired that the static eliminator be less affected by contamination of the measuring section 1a including the analyte receptacles P2. This static eliminator 13 is so positioned around the sample turntable 2 that its charge emitting surface is directed at the center of rotation of the sample turntable 2.

The static eliminator 13 may be placed close to the reading device 12, but the present invention is not limited to this arrangement. Where the sample turntable 2 is located within the receiving wall 2a, the static eliminator 13 should be placed opposite to the peripheral walls of some analyte receptacles P2 held on the sample turntable 2, through the opening 2c formed in the receiving wall 2a.

Enclosure 1b

The enclosure 1b accommodates the various components of the aforementioned measuring section 1a and includes the first cover member 31, the second cover member 32, and the third cover member 33. Of these members, the first cover member 31 is mounted so as to open and close the top portion of the sample turntable 2. The second cover member 32 is mounted to open and close the top portion of the reagent turntable 4. The third cover member 33 provides an openable cover over all of the sample turntable 2, dilution turntable 3, reagent turntable 4, reaction turntable 5, sample diluting pipette 6, sampling pipette 7, first reagent pipette 8, and second reagent pipette 9. The first cover member 31 and second cover member 32 can open and close the top portions of the sample turntable 2 and reagent turntable 4, respectively, independently of the third cover member 33.

Open/close sensors 31a, 32a, 33a are mounted on the first cover member 31, second cover member 32, and third cover member 33, respectively, to detect whether these cover members are open or closed. If it is possible to detect whether these cover members 31, 32, 33 are open or closed, the open/close sensors 31a, 32a, and 33a may be of any construction type. FIG. 2 shows an operational state where the first cover member 31 and second cover member 32 are closed and where the third cover member 33 is closed as indicated by the dotted and dashed line.

Control Section 1c

Figure 3:
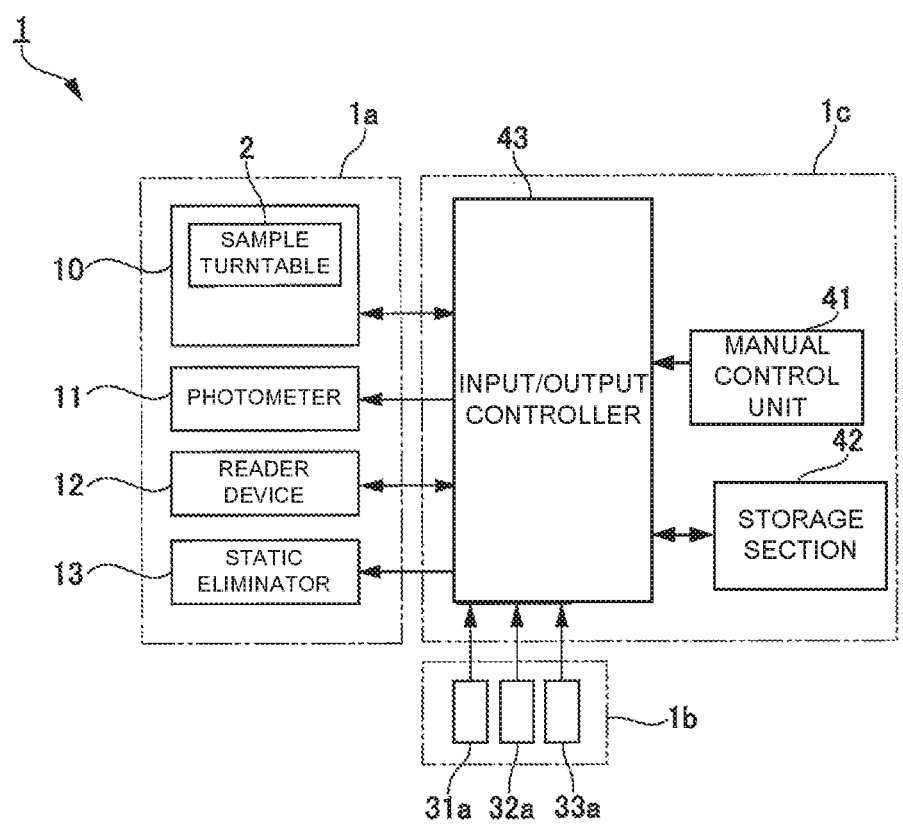
FIG. 3 is a block diagram of the automated analyzer of FIGS. 1 and 2.

The control section 1c is connected with the above-described various components of the measuring section 1a and controls the operations of these components. The control section 1c is a terminal device used for control purposes such as a personal computer. FIG. 3 is a block diagram of the automated analyzer 1 associated with the first embodiment. As shown in this figure, the control section 1c includes the manual control unit 41, a storage section 42, and an input/output controller 43. These components are described in detail below.

<Manual Control Unit 41>

The manual control unit 41 accepts a user's input on operations of the automated analyzer 1 and outputs an input signal to the input/output controller 43. A mouse, a keyboard, a touch panel on a display unit, or the like is used as the manual control unit 41.

<Storage Section 42>

The storage section 42 is made of a mass storage device such as an HDD (hard disk drive) or a semiconductor memory and stores programs executed by the input/output controller 43, parameters, calibration lines, measurement results, input actions performed through the manual input unit 41, and so on.

<Input/Output Controller 43>

The input/output controller 43 is connected with the manual control unit 41 and the storage section 42 and also with drive mechanisms 10 of the measuring section 1a, the photometer 11, the reader device 12, and the static eliminator 13. Furthermore, the input/output controller 43 is connected with the open/close sensors 31a, 32a, and 33a respectively mounted on the first cover member 31, the second cover member 32, and the third cover member 33 of the enclosure 1b.

The input/output controller 43 controls the operational timings of the drive mechanisms 10 of the measuring section 1a in response to input actions performed through the manual control unit 41 and controls the timing of measurement of absorbance made by the photometer 11. Thus, the controller 43 dilutes the analytes in the analyte receptacles P2 held on the sample turntable 2 to a desired concentration, mixes their diluted analytes with reagents to induce reactions, and measures the absorbances of the resulting reaction liquids by the photometer 11.

In addition, the input/output controller 43 controls the operational timing of the sample turntable 2 of the drive mechanisms 10 in response to an input action made via the manual control unit 41 and in response to input signals from the open/close sensors 31a, 33a. The input/output controller 43 also controls the operations of the reader device 12 and static eliminator 13. Especially, the input/output controller 43 causes the reader device 12 to read the successive sets of identification information of the analyte receptacles P2 while carrying the analyte receptacles P2 by the operation of the sample turntable 2. In synchronism with this reading, the static eliminator 13 is operated to eliminate static charge on the analyte receptacles P2.

The input/output controller 43 described so far is made of a computer, for example, such as a microcomputer, equipped with a CPU (central processing unit), a ROM (read only memory), and a RAM (random access memory).

Specific examples of operational timings of the drive mechanisms 10 of the measuring section 1a, the timing of measurement made by the photometer 11, and the operational timings of the reader device 12 and static eliminator 13 which are achieved by the input/output controller 43 described thus far are described in relation to an automated analysis method.

<<Automated Analysis Method>>

Figure 4:
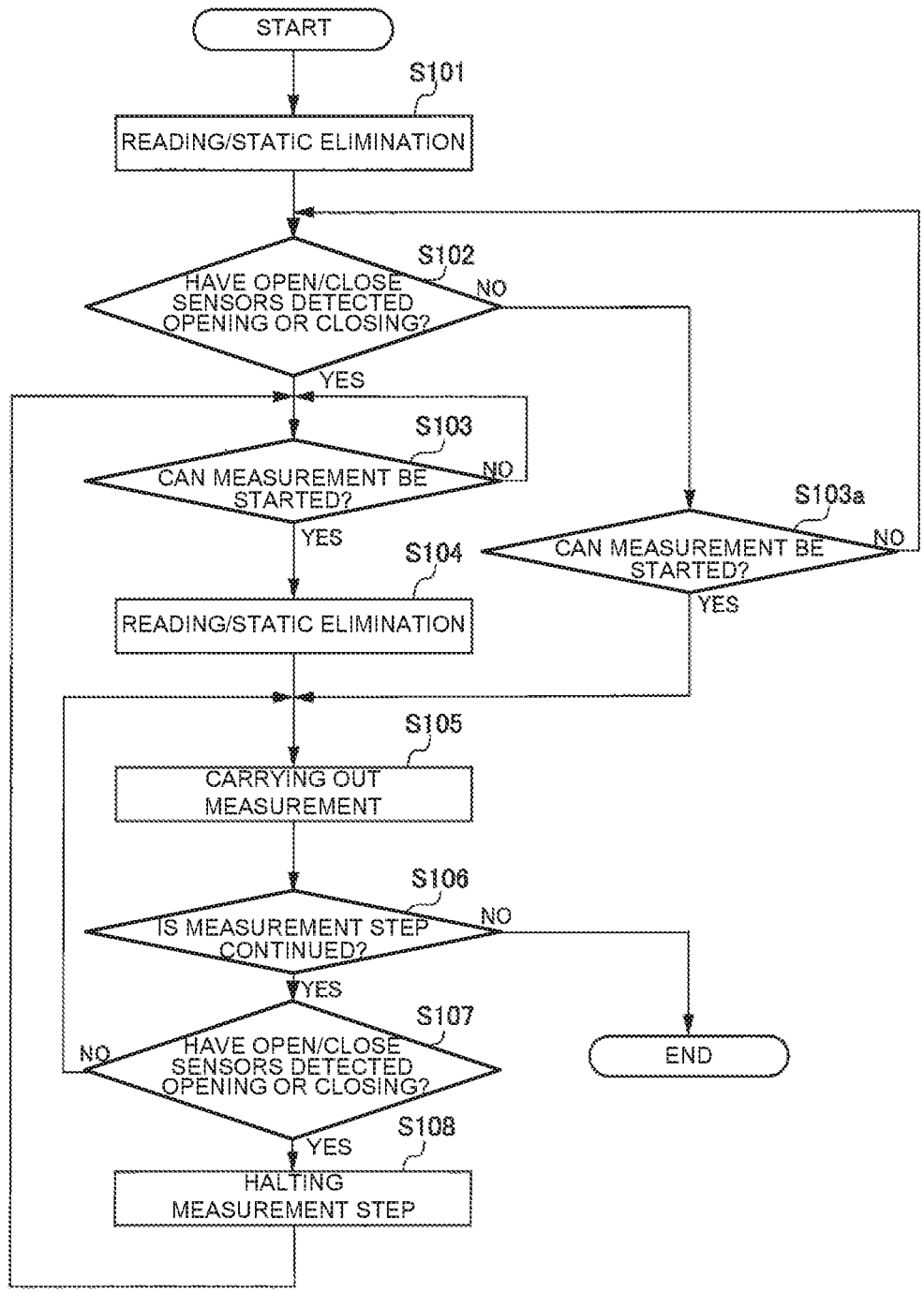
FIG. 4 is a flowchart illustrating an automated analysis method associated with the first embodiment.

FIG. 4 is a flowchart illustrating an automated analysis method associated with the first embodiment and depicting a procedure for the automated analysis method using the automated analyzer 1 of the first embodiment. The automated analysis method executed by the input/output controller 43 of the automated analyzer 1 is next described by referring to the flowchart of FIG. 4 and also to FIGS. 1-3.

Step S101

In step S101, when the automated analyzer 1 is powered ON, the input/output device 43 carries out reading of the identification information of the analyte receptacles P2 and static elimination. At this time, the input/output controller 43 rotates the sample turntable 2 of the drive mechanisms 10 at least once. Consequently, the analyte receptacles P2 held on the sample turntable 2 are rotationally carried such that they make at least one turn circumferentially of the sample turntable 2.

In synchronism with the operation of the sample turntable 2 as described so far, the input/output controller 43 causes the reader device 12 to perform a reading operation on the analyte receptacles P2 held on the sample turntable 2. In particular, the reader device 12 reads the successive sets of identification information of all the analyte receptacles P2 which are placed so as to face the reader device 12. All the sets of identification information read by the reader device 12 are stored in memory in association with the positions in the sample turntable 2 where the analyte receptacles P2 are held.

In synchronism with the successive reading by the reader device 12, the input/output controller 43 carries out elimination of static charge on the analyte receptacles P2 held on the sample turntable 2. The static eliminator 13 may be operated continuously during at least one revolution of the sample turntable 2. As a result, static charge on all the analyte receptacles P2 facing the static eliminator 13 out of the analyte receptacles P2 held on the sample turntable 2 is electrically neutralized and eliminated.

By performing this step S101, if the power supply is OFF and the analyte receptacles P2 on the sample turntable 2 have been replaced by new ones, reading of the identification information of the new analyte receptacles P2 and static elimination are carried out.

Step S102

In step S102, the input/output controller 43 makes a decision as to whether the open/close sensors 31a and 33a have detected opening or closing. In this specific example, the input/output controller 43 makes a decision as to whether the open/close sensor 31a has detected that the first cover member 31 has entered an open state from a closed state, whether the open/close sensor 33a has detected that the third cover member 33 has entered an open state from a closed state, or whether both have been detected. If the decision is YES, indicating that opening or closing is detected, control goes to the next step S103. If the decision is NO, indicating that opening or closing is not detected, control proceeds to the next step S103a. This decision is similarly made if the open/close sensors 31a and 33a have detected opening or closing after an input to replace the analyte receptacles P2 is made via the manual control unit 41.

Step S103

In step S103, the input/output controller 43 makes a decision as to whether a measurement can be started, depending on an input action performed, for example, via the manual control device 41. If an input is provided for giving an instruction to start a measurement, it is determined that a measurement can be started (YES). Alternatively, if it is detected from all the open/close sensors 31a, 32a, and 33a that the first cover member 31, second cover member 32, and third cover member 33 are in their closed state after an input is provided for giving an instruction to start a measurement in response to an input action performed via the manual control unit 41, it may be determined that a measurement can be started (YES).

The decision step (S103) is repeated until it is determined that a measurement can be started (YES). If it is determined that a measurement can be started (YES), control goes to step S104.

Step S104

In step S104, the input/output controller 43 carries out reading of identification information of each analyte receptacle P2 as well as static elimination. This step S104 is performed similarly to step S101 already described except for the following respects. All sets of identification information read by the reader device 12 are associated with the positions at which the analyte receptacles P2 are held on the sample turntable 2. Then, the sets of identification information are made to overwrite the identification information already in storage and are stored in memory.

If opening or closing is detected at step S102, there is a possibility that an exchange or addition of analyte receptacles P2 on the sample turntable 2 may have occurred. However, by performing this step S104, if opening or closing is detected at step S102, reading of identification information of the analyte receptacles P2 is always carried out. At the same time, static elimination is performed.

Step 103a

On the other hand, in step S103a, the input/output controller 43 makes a decision as to whether a measurement can be started, in the same way as step S103. However, in this step S103a, control goes back to step S102 until it is determined that a measurement can be started (YES). The decision as to whether the open/close sensors 31a and 33a have detected opening or closing is repeated until a state is reached where a measurement can be started.

If the decision at step S103a is YES, indicating that a measurement can be started, control goes to step S105. Then, control proceeds from the present step S103a to the next step S105 only when a state is reached where a measurement can be started without detecting opening or closing in step S102. That is, if opening or closing is detected in step S102 before it is determined that a measurement can be started (YES), then the previous step S104 (reading and static elimination) is carried out.

Step S105

In step S105, the input/output controller 43 carries out a measurement. At this time, the input/output controller 43 controls the operational timings of the drive mechanisms 10 of the measuring section 1a, based on an input action made via the manual control unit 41 and on a measurement program stored in the storage section 42, and controls the timing at which absorbances are measured by the photometer 11. Consequently, the analyte aliquots in the analyte receptacles P2 held on the sample turntable 2 are diluted to a given concentration. Each diluted analyte aliquot is mixed with a reagent to induce a reaction. The absorbance of the resulting reaction liquid is measured by the photometer 11.

In this measurement sequence, the liquid level sensor mounted to the sample diluting pipette 6 detects the liquid level of the analyte in each analyte receptacle P2 held in position on the sample turntable 2. The tip of a pipette is inserted into a given depth below the liquid level of the analyte and a given amount of analyte is drawn in from the tip of the pipette filled with a diluent. The sample diluting pipette 6 dispenses the aspirated analyte as aliquots into the dilution receptacles P3 placed in position on the dilution turntable.

Step S106

In step S106, the input/output controller 43 makes a decision as to whether the measurement step is continued. At this time, if any input to end the measurement step is not entered through the manual control unit 41, or if measurement of all the analyte aliquots is not complete, the input/output controller 43 determines that the measurement step should be continued (YES). Control goes to the next step S107. On the other hand, if an input to end the measurement step is entered, for example, through the manual control unit 41, or if measurement of all the analyte aliquots is complete, it is determined that the measurement step should not be continued (NO), and the present processing sequence is ended.

Step S107

In step S107, the input/output controller 43 makes a decision as to whether the open/close sensors 31a and 33a have detected opening or closing. This decision is carried out in the same manner as the above-described step S102. If the result of the decision is that opening or closing is detected (YES), control goes to the next step S108. On the other hand, if the result of the decision is that opening or closing is not detected (NO), control returns to step S105 and the measurement step is continued.

Step S108

In step S108, the input/output controller 43 halts the measurement step on the assumption that the drive mechanisms 10 of the measuring section 1a are in a given condition. Control then proceeds back to step S103 and the subsequent steps are repeated. If opening or closing is detected in step S107, then there is a possibility that an exchange or addition of analyte receptacles P2 may have taken place on the sample turntable 2 even during the measurement step. However, by executing this step S108 and the subsequent step S103, if opening or closing is detected in step S107, then it follows that reading of the identification information of the analyte receptacles P2 is always executed. At the same time, static elimination is conducted. That is, if the measurement step is in progress, reading and static elimination of step S104 are performed whenever opening or closing is detected in step S107. Then, the measurement step of step S105 is performed.

<<Advantages of First Embodiment>>

According to the first embodiment described so far, when the identification information of the analyte receptacles P2 carried by the sample turntable 2 is read by the reader device 12, static elimination from the analyte receptacles P2 is carried out by the static eliminator 13. Therefore, the liquid level of analyte received in each analyte receptacle P2 can be detected accurately, for example, by the liquid level sensor of the sample diluting pipette 6 and thus an accurate amount of analyte can be aspirated from the tip of the sample diluting pipette 6 without drawing in gas. In addition, adsorption of air bubbles onto the inner walls of the analyte receptacles P2 is prevented. This also assures that the accuracy of the amount of analyte aspirated by the sample diluting pipette 6 can be enhanced. As a result, the analysis accuracy of the automated analyzer 1 can be improved.

Furthermore, static elimination is carried out in synchronism with reading of identification information and so all the analyte receptacles P2 held on the sample turntable 2 are subjected to static elimination at the same time. If each individual analyte receptacle P2 is subjected to static elimination separately, the sample turntable 2 would need be driven specially for that purpose. Also, the static eliminator 13 would need be operated for a long time. As a result, the operation of the analyzer is not complicated. Furthermore, consumption of the static eliminator 13 is suppressed. Hence, the instrument and maintenance costs can be suppressed.

Additionally, if the measurement step is underway, and if an exchange or addition of analyte receptacles P2 might have taken place because the open/close sensors 31a and 33a have detected opening or closing, the aforementioned reading and static elimination are carried out each time.

Then, a measurement step is performed. Accordingly, a measurement step is performed after static elimination on the analyte receptacles P2 has been reliably completed. Consequently, the accuracy of analysis of the automated analyzer 1 can be enhanced for measurements on all the analytes.

Modification of First Embodiment

In the above-described first embodiment, there is described the configuration of the automated analyzer 1 having the sample turntable 2 to which the reader device 12 and the static eliminator 13 are mounted. In a modification of the first embodiment, the reader device 12 and the static eliminator 13 are mounted to the reagent turntable 4 rather than to the sample turntable 2. Alternatively, the reader device 12 and the static eliminator 13 may be mounted to each of the sample turntable 2 and the reagent turntable 4.

In the case of this configuration, each individual reagent receptacle P4 held on the reagent turntable 4 has unique identification information. It is assumed that the identification information is a barcode, for example, and attached to the sidewall of each reagent receptacle P4.

It is also assumed that the reader device 12 and static eliminator 13 mounted to the reagent turntable 4 are disposed inside the cylindrical thermostat bath 4a in which the reagent turntable 4 is received and that the illumination head of the reader device 12 and the charge emissive surface of the static eliminator 13 are disposed opposite to the sidewalls of the reagent receptacles P4.

Also in this case, the input/output controller 43 of the first embodiment practices the automated analysis method in response to an input from the open/close sensor 32a of the second cover member 32 providing a cover over the reagent turntable 4, an input from the open/close sensor 33a mounted to the third cover member 33, and an input from the manual control unit 41.

At this time, a procedure similar to the procedure of the flowchart of FIG. 4 is carried out in response to input signals from the open/close sensors 32a, 33a, and manual control unit 41 independently of the procedure illustrated in the flowchart of FIG. 4.

Consequently, similar advantages can be had from the reagent receptacles P4 held on the reagent turntable 4. Especially, where the reader device 12 and the static eliminator 13 are installed on each of the sample turntable 2 and the reagent turntable 4, similar advantages can be derived from both analyte receptacles P2 and reagent receptacles P4. As a consequence, the accuracy of analysis can be enhanced further.

Second Embodiment

<<Automated Analyzer>>

Figure 5:
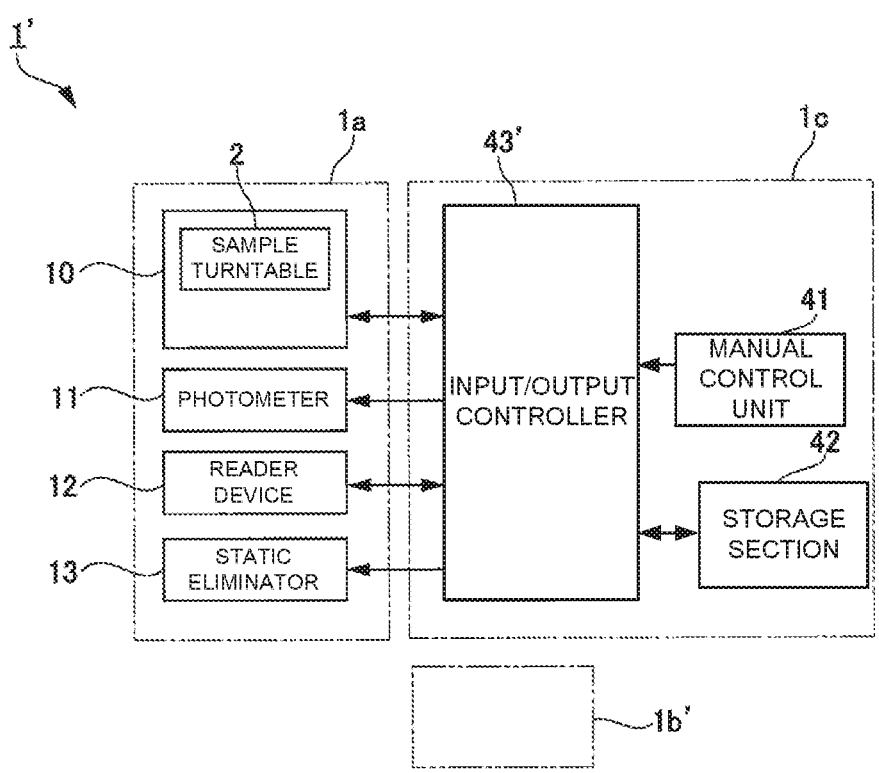
FIG. 5 is a block diagram of an automated analyzer associated with a second embodiment.

FIG. 5 is a block diagram of an automated analyzer 1' associated with a second embodiment. One difference of the automated analyzer 1' of FIG. 5 from the automated analyzer 1 of the first embodiment is that the cover members of the enclosure 1b' do not have their respective open/close sensors 31a, 32a, and 33a. Another difference lies in parts of processing performed by the input/output controller 43'.

<<Automated Analysis Method>>

Figure 6:
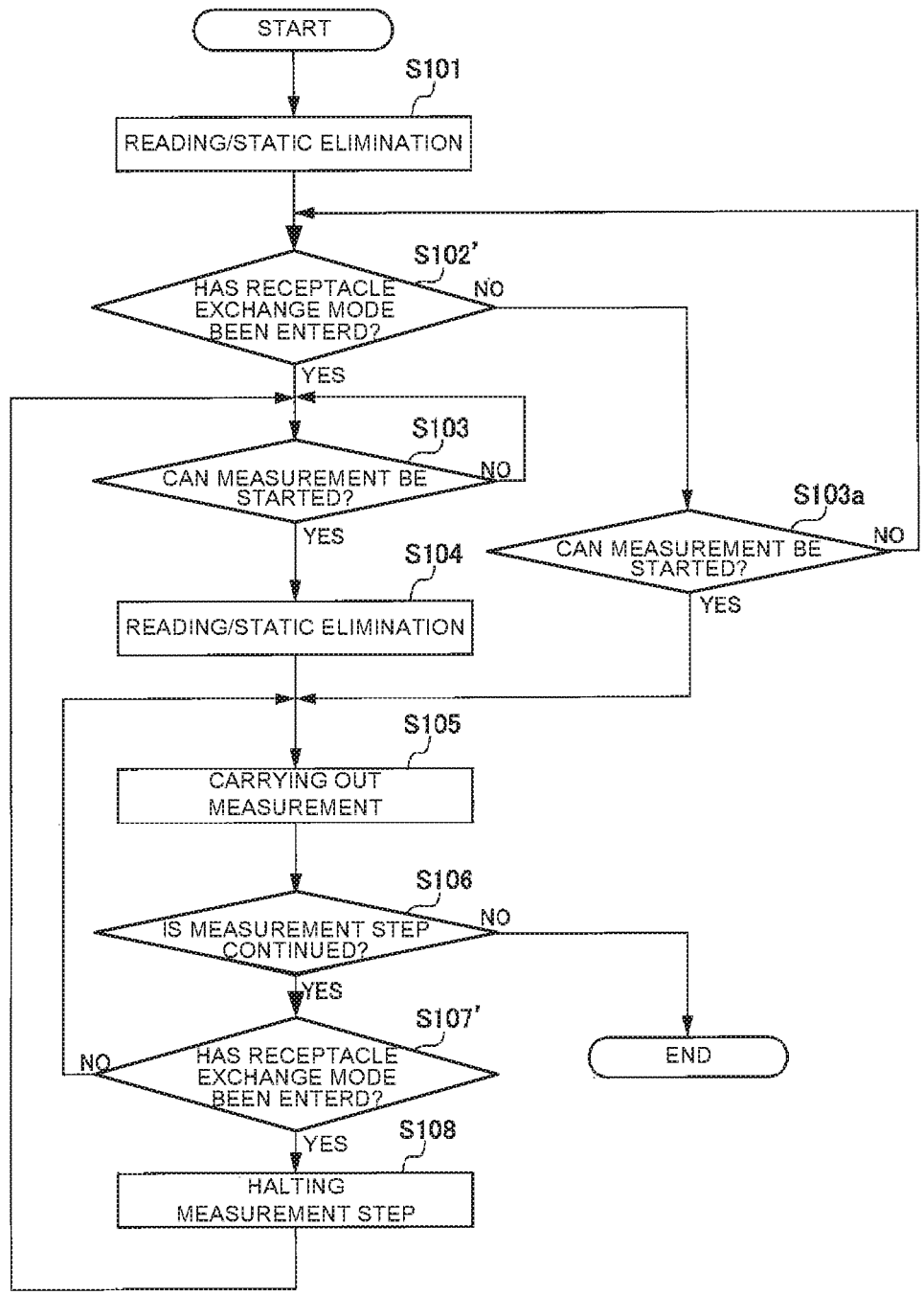
FIG. 6 is a flowchart illustrating an automated analysis method associated with the second embodiment.

FIG. 6 is a flowchart illustrating an automated analysis method associated with the second embodiment. This automated analysis method depicted in FIG. 6 is similar to the automated analysis method of the first embodiment except for decisions made in steps S102' and S107' which will be described below.

\<Step S102'\>

In step S102', the input/output controller 43' makes a decision as to whether a receptacle exchange mode has been entered. At this time, if an input is made in response to an input action made through the manual control unit 41 to enter the receptacle exchange mode, meaning that the analyte receptacles will be exchanged, it is determined that the receptacle exchange mode (YES) is established and control goes to the next step S103. On the other hand, if the decision is NO, indicating that the receptacle exchange mode is not established, control proceeds to the next step S103a.

\<Step 107'\>

In step S107', the input/output controller 43' makes a decision as to whether the exchange mode is established. This decision is carried out similarly to the previous step S102'. If the decision is YES, indicating that the exchange mode is established, control goes to the next step S108. On the other hand, if the decision is NO, indicating that the exchange mode is not established, control goes back to step S105 and the measurement step is continued.

<<Advantages of Second Embodiment>>

The configuration described so far can yield advantages similar to those provided by the automated analyzer 1 and automated analysis method of the first embodiment. Especially, in the present second embodiment, if the receptacle exchange mode is established in response to an input action made via the manual control unit 41, reading and static elimination are done. Therefore, only when it is assured that a work for replacing the analyte receptacles P2 in the sample turntable 2 has been done, reading and static elimination are carried out. As a result, extra execution of reading and static elimination can be eliminated as compared with the first embodiment.

Modification of Second Embodiment

In the above second embodiment, there is described the configuration of the automated analyzer 1' having the sample turntable 2 on which the reader device 12 and the static eliminator 13 are installed. In a modification of the second embodiment, the reader device 12 and the static eliminator 13 are installed also to the reagent turntable 4, in the same manner as in the above-described modification of the first embodiment. This modification can offer similar advantages.

The invention claimed is:

1. An apparatus comprising:
   a receptacle carrier mechanism operative to hold a plurality of receptacles storing liquid and to carry the plurality of receptacles in a given direction;
   a reader device to read identification information of the plurality of receptacles, which are storing the liquid, carried by the receptacle carrier mechanism;
   a static eliminator to eliminate static charge on the plurality of receptacles, which are storing the liquid, carried by the receptacle carrier mechanism; and
   an input/output controller programmed or configured to:
   rotate the receptacle carrier mechanism at least once, wherein the plurality of receptacles held on the receptacle carrier mechanism are rotationally carried to make at least one turn circumferentially;
   during a rotation of the receptacle carrier mechanism, cause the static eliminator to carry out an elimination of the static charge on the plurality of receptacles, which are storing the liquid, in synchronism with successive reading by the reader device of the identification information of the plurality of receptacles, which are storing the liquid, carried by the receptacle carrier mechanism, wherein the static eliminator is operated continuously during rotation of the receptacle carrier mechanism; and
   store, in memory, the identification information of the plurality of receptacles in association with positions of the plurality of receptacles in the receptacle carrier mechanism.

2. The apparatus as set forth in claim 1, further comprising:
   an enclosure equipped with a cover member that provides a cover over said receptacle carrier mechanism; and
   an open/close sensor mounted on the cover member,
   wherein said input/output controller is programmed or configured to:
   cause said reader device to carry out said reading and said static eliminator to carry out said elimination of the static charge whenever the open/close sensor detects opening or closing of the cover member.

3. The apparatus as set forth in claim 1, further comprising:
   a manual control unit connected with said input/output controller, and wherein the input/output controller is programmed or configured to:
   cause said reader device to carry out said reading and said static eliminator to carry out said elimination of the static charge whenever an input is made through the manual control unit to enter a receptacle exchange mode in which the receptacles held in said receptacle carrier mechanism are exchanged.

4. The apparatus as set forth in claim 1, wherein said input/output controller is programmed or configured to:
   cause said reader device to carry out said reading and said static eliminator to carry out said elimination of the static charge if it is determined that a measurement step can be started while said receptacle carrier mechanism is in operation.

5. The apparatus as set forth in claim 1, wherein said input/output controller is programmed or configured to:
   cause said reader device to carry out said reading and said static eliminator to carry out said elimination of the static charge in response to activation of a power supply.

6. The apparatus as set forth in claim 1, wherein the receptacle carrier mechanism comprises:
   a sample turntable holding a first plurality of receptacles, one or more receptacles of the first plurality of receptacles storing an analyte to be examined; and
   a reagent turntable holding a second plurality of receptacles, one or more receptacles of the second plurality of receptacles storing a reagent, and wherein said reader device and said static eliminator are mounted on at least one of the sample turntable and the reagent turntable.

7. The apparatus as set forth in claim 1, further comprising:
   a pipette for drawing in the liquid from within a selected one of the plurality of receptacles held by said receptacle carrier mechanism; and
   a liquid level detecting mechanism for detecting a tip of the pipette and a level of the liquid stored in the selected receptacle,
   wherein said input/output controller causes the tip of the pipette to be immersed to a given depth in the liquid within the selected receptacle on the basis of the level of the liquid detected by the liquid level detecting mechanism.

8. The apparatus as set forth in claim 1, wherein said input/output controller is further programmed or configured to:
  determine whether a measurement step can be started, wherein, when determining whether the measurement step can be started, said input/output controller is programmed or configured to:
    determine whether a cover member is in a closed state based on an input signal from one or more open/close sensors.

9. The apparatus as set forth in claim 8, wherein the rotation of the receptacle carrier mechanism is a first rotation of the receptacle carrier mechanism, wherein the at least one turn circumferentially is at least one first turn circumferentially, and wherein said input/output controller is further programmed or configured to:
  rotate the receptacle carrier mechanism based on determining that the measurement step can be started, wherein the plurality of receptacles held on the receptacle carrier mechanism are rotationally carried to make at least one second turn circumferentially;
  during a second rotation of the receptacle carrier mechanism, cause the static eliminator to carry out an elimination of a static charge on the plurality of receptacles in synchronism with successive reading by the reader device of second identification information of the plurality of receptacles carried by the receptacle carrier mechanism, wherein the static eliminator is operated continuously during the second rotation of the receptacle carrier mechanism; and
  store, in the memory, the second identification information of the plurality of receptacles in association with positions of the plurality of receptacles in the receptacle carrier mechanism, wherein, when storing the second identification information of the plurality of receptacles in association with positions of the plurality of receptacles in the receptacle carrier mechanism, the input/output controller is programmed or configured to:
    overwrite the identification information of the plurality of receptacles previously stored in the memory with the second identification information of the plurality of receptacles.

10. The apparatus as set forth in claim 1, wherein the receptacle carrier mechanism comprises:
  a sample turntable holding a first plurality of receptacles, one or more receptacles of the first plurality of receptacles storing an analyte to be examined; and
  wherein said input/output controller is further programmed or configured to:
    carry out a measurement step based on determining that the measurement step can be started, wherein, when carrying out the measurement, the input/output controller is programmed or configured to:
  control a liquid level sensor to detect a liquid level of the analyte in each of the one or more receptacles of the first plurality of receptacles.

* * * * *